(12) United States Patent
Liu et al.

(10) Patent No.: US 10,485,426 B2
(45) Date of Patent: Nov. 26, 2019

(54) DEVICE HAVING HEALTH DETECTING FUNCTION, DISPLAY APPARATUS, SYSTEM AND HEALTH DETECTING METHOD (71) Applicant: BOE TECHNOLOGY GROUP CO., LTD., Beijing (CN)

(72) Inventors: Jiantao Liu, Beijing (CN); Xiaolei Cui, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 269 days.

(21) Appl. No.: 15/112,561

(22) PCT Filed: Nov. 11, 2015

(86) PCT No.: PCT/CN2015/094325
§ 371 (c)(1),
(2) Date: Jul. 19, 2016

(87) PCT Pub. No.: WO2016/179985
PCT Pub. Date: Nov. 17, 2016

(65) Prior Publication Data
US 2017/0143211 A1 May 25, 2017

(30) Foreign Application Priority Data
May 11, 2015 (CN) .......................... 2015 1 0236951

(51) Int. Cl.
H04N 5/232 (2006.01)
A61B 5/00 (2006.01)
(Continued)

(52) U.S. Cl.
CPC .............. A61B 5/0077 (2013.01); A61B 5/01 (2013.01); A61B 5/015 (2013.01); A61B 5/021 (2013.01);
(Continued)

(58) Field of Classification Search
CPC ........ G06T 2207/30201; G06K 9/0061; H04N 5/23219
See application file for complete search history.

(56) References Cited

U.S. PATENT DOCUMENTS 9,729,865 B1* 8/2017 Kuo .................... G06K 9/00268
2006/0067573 A1* 3/2006 Parr .................... G06K 9/00201
382/154
(Continued)

FOREIGN PATENT DOCUMENTS

CN 101247760 A 8/2008
CN 102131064 A 7/2011
(Continued)

OTHER PUBLICATIONS

Office Action issued by the Chinese Patent Office dated Jan. 5, 2017.
(Continued)

Primary Examiner — Michael J D Abreu
(74) Attorney, Agent, or Firm — Dilworth & Barrese, LLP.; Michael J. Musella, Esq.

(57) ABSTRACT

A device having a health detecting function (10), a display apparatus (1), a system and a health detecting method are provided, capable of monitoring physical condition and discovering an illness in time. The device (10) having the health detecting function includes a processing module (101) and a storage module (102). The processing module (101) is configured for receiving image information of a detected person and storing the image information in the storage module (102). The image information of the detected person includes a part image of the detected person and an acquiring time and an ambient light intensity when acquiring the part image. change information of the part image of the detected person is obtained according to the part image of the detected person and a reference part image in reference part image information obtained from the storage module in
(Continued)

a case where the ambient light intensity is greater than a predetermined value, and current physical health information of the detected person is obtained according to the change information of the part image. The storage module (102) is configured for storing the reference part image information, the reference part image information including reference a part image of the detected person accumulated before the acquiring time and/or a healthy reference part image based on age.

16 Claims, 8 Drawing Sheets

(51) Int. Cl.
    *A61B 5/01* (2006.01)
    *A61B 5/021* (2006.01)
    *A61B 5/024* (2006.01)
    *A61B 5/20* (2006.01)

(52) U.S. Cl.
    CPC ........ *A61B 5/02438* (2013.01); *A61B 5/4854* (2013.01); *A61B 5/742* (2013.01); *A61B 5/20* (2013.01); *A61B 5/40* (2013.01); *A61B 5/42* (2013.01); *A61B 5/44* (2013.01); *A61B 5/6801* (2013.01); *A61B 5/743* (2013.01); *A61B 5/7435* (2013.01); *A61B 2560/0242* (2013.01); *A61B 2576/02* (2013.01)

(56) References Cited

U.S. PATENT DOCUMENTS

| | | | |
|---|---|---|---|
| 2008/0317339 A1* | 12/2008 | Steinberg | G06K 9/0061 |
| | | | 382/167 |
| 2009/0225102 A1 | 9/2009 | Okubo et al. | |
| 2010/0280350 A1 | 11/2010 | Zhang | |
| 2015/0261996 A1* | 9/2015 | Kim | G06K 9/00255 |
| | | | 348/14.03 |
| 2016/0360970 A1* | 12/2016 | Tzvieli | A61B 5/015 |

FOREIGN PATENT DOCUMENTS

| | | |
|---|---|---|
| CN | 103690149 A | 4/2014 |
| CN | 103735253 A | 4/2014 |
| CN | 104873172 A | 9/2015 |
| WO | 2009104583 A1 | 8/2009 |

OTHER PUBLICATIONS

Search Report and Written Opinion dated Feb. 15, 2016 from State Intellectual Property Office of the P.R. China.
Office Action issued by the Chinese Patent Office dated Aug. 1, 2017.

* cited by examiner

| receiving image information of a detected person and storing the image information in the storage module 102 by a processing module 101 of the device 10 having the health detecting function, wherein the image information of the detected person includes a part image of the detected person and an acquiring time and an ambient light intensity when acquiring the part image | S01 |

| obtaining change information of the part image of the detected person by the processing module 101 according to the part image of the detected person and a reference part image in reference part image information in a case where the ambient light intensity is greater than a predetermined value | S02 |

| Obtaining a current physical health information of the detected person by the processing module 101 according to the change information of the part image and transmitting to a display module, for displaying in the display module | S03 |

FIG. 13 ial sub-part images based on an accuracy mode provided
DEVICE HAVING HEALTH DETECTING FUNCTION, DISPLAY APPARATUS, SYSTEM AND HEALTH DETECTING METHOD

TECHNICAL FIELD

Embodiments of the present disclosure relate to a device having a health detecting function, a display apparatus, a system and a health detecting method.

BACKGROUND

Along with social progress and improvement of people's living standard, personal health condition has become a hot issue attracting more and more attention. However, how to monitor a physical condition and discover an illness in time, so as to take a corresponding countermeasure, has become a hot point in current research and development.

Nowadays, people have more and more pressures in working and living, with which more and more ailments, problems and the like are brought to a human body, but these potential diseases attract little attention. In fact, a lot of diseases have a number of external manifestations on human body at early stage, and if the warning information transferred by the body is noticed in time, and is conditioned or treated in time, a lot of diseases can be cured in the beginning.

SUMMARY

An embodiment of the present disclosure provides a device having a health detecting function, including a processing module and a storage module; wherein, the processing module is configured for receiving image information of a detected person and storing the image information in the storage module, the image information of the detected person including a part image of the detected person and an acquiring time and an ambient light intensity when acquiring the part image; obtaining change information of the part image of the detected person according to the part image of the detected person and a reference part image in reference part image information obtained from the storage module, in a case where the ambient light intensity is greater than a predetermined value; and obtaining current physical health information of the detected person according to the change information of the part image; the storage module is configured for storing the reference part image information, the reference part image information including a reference part image of the detected person accumulated before the acquiring time and/or a healthy reference part image based on age.

Another embodiment of the present disclosure provides a display apparatus, including a display module and the above described device having the health detecting function, wherein, the processing module of the device having the health detecting function transmits current physical health information of a detected person to the display module for displaying.

Yet another embodiment of the present disclosure provides a system having a health detecting function, including a display apparatus and a cloud server; wherein, the display apparatus includes a display module; the cloud server includes the above described device having the health detecting function, the processing module of the device having the health detecting function being configured for transmitting current physical health information of the detected person to the display module for displaying.

Yet another embodiment of the present disclosure provides a health detecting method, including: receiving image information of a detected person and storing the image information; wherein, the image information of the detected person includes a part image of the detected person and an acquiring time and an ambient light intensity when acquiring the part image; obtaining change information of the part image of the detected person according to the part image of the detected person and a reference part image in reference part image information in a case where the ambient light intensity is greater than a predetermined value; obtaining current physical health information of the detected person according to the change information of the part image, and transmitting the current physical health information of the detected person to a display module, so as to display in the display module; wherein, the reference part image information includes a reference part image of the detected person accumulated before the acquiring time and/or a healthy reference part image based on age.

BRIEF DESCRIPTION OF THE DRAWINGS

In order to clearly illustrate the technical solution in the embodiments of the present disclosure, the drawings necessary for description of the embodiments or the related prior art will be briefly described hereinafter; it is obvious that the described drawings are only related to some embodiments of the present disclosure, and thus are not limitative of the present disclosure.

DETAILED DESCRIPTION

The technical solutions of the embodiments of the present disclosure will be described in a clearly and fully understandable way in connection with the drawings. It is obvious that the described embodiments are just a part but not all of the embodiments of the present disclosure. Based on the described embodiments of the present disclosure, those ordinarily skilled in the art can obtain other embodiment(s), without any inventive work, which should be within the protective scope of the present disclosure.

Embodiments of the present disclosure provide a device having a health detecting function, a display apparatus, a system and a health detecting method. A received part image of a detected person and a reference part image in reference part image information obtained from a storage module are compared and analyzed by a processing module, so as to obtain change information of the part image of the detected person. And, current physical health information of the detected person is obtained on the basis of theory of traditional Chinese medicine. Then, the physical health information of the detected person is transmitted to a display module for displaying in the display module, so that a physical condition of the detected person is monitored, and thus an illness may be discovered in time.

Figure 1:
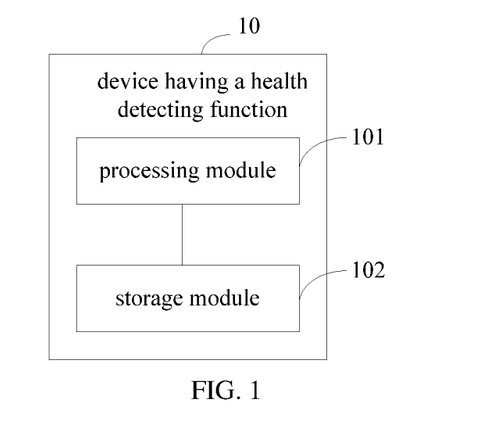
FIG. 1 is a block diagram of a device having a health detecting function provided by an embodiment of the present disclosure.

An embodiment of the present disclosure provides a device 10 having a health detecting function, as shown in FIG. 1, the device 10 having the health detecting function includes a processing module 101 and a storage module 102; the processing module 101 is configured for receiving image information of a detected person and storing the image information in the storage module 102, wherein, the image information of the detected person including a part image of the detected person and an acquiring time and an ambient light intensity when acquiring the part image; obtaining change information of the part image of the detected person according to the part image of the detected person and a reference part image in reference part image information obtained from the storage module 102 in a case where the ambient light intensity is greater than a predetermined value, and obtaining current physical health information of the detected person according to the change information of the part image and transmitting it to a display module. The storage module 102 is configured for storing the reference part image information, the reference part image information including reference part images of the detected person accumulated before the acquiring time and/or healthy reference part images based on ages.

Firstly, it should be noted that the change information of the part image of the detected person is obtained according to the part image of the detected person and the reference part image, that is, change information of the part image of the detected person is obtained by comparing and analyzing the part image of the detected person with the reference part image.

On such basis, those skilled in the art should understand that, comparing and analyzing are generally based on a same part, and therefore, in the embodiment of the present disclosure, the reference part image in reference part image information and the part image in image information of the detected person are images of the same part.

Herein, the part image of the detected person is not limited. It may be a facial image, or an image of four limbs such as a palm, an arm, and a leg and so on.

Secondly, a photographing module independent of the device 10 having the health detecting function may be configured for acquiring a part image of a detected person, and then transmitting image information of the detected person including the part image, an ambient light intensity and an acquiring time to the processing module 101 of the device 10 having the health detecting function.

Thirdly, the reference part image in the reference part image information may include reference part images of the detected person accumulated before the acquiring time. For example, all reference part images of the same detected person before the acquiring time are stored in the storage module 102. On such basis, when the part image of the detected person are compared and analyzed with the reference part image in reference part image information obtained from the storage module 102, a healthiest reference part image in the reference part image information may be selected for comparing and analyzing, or one or more reference part images close to the acquiring time may be compared and analyzed with, so as to obtain change information of the part image of the detected person in a certain period, and of course, all reference part images in the reference part image information may be also compared and analyzed with, so as to obtain a curve of changes, based on which current physical health condition of the detected person may be determined.

Of course, the reference part image in the reference part image information may further include healthy reference part images based on ages and further based on gender, and in this case, the part image of the detected person may be directly compared and analyzed with the healthy reference part image.

In addition, the two cases described above may be compared and analyzed at the same time, which will not be repeated here.

Fourthly, those skilled in the art should know that, based on theory of traditional Chinese medicine, current physical health condition of the detected person may be preliminarily determined according to change information of images of different parts of a body, such as color changes, wrinkles, size changes and other information.

The embodiment of the present disclosure provides a device 10 having a health detecting function. A received part image of the detected person and a reference part image in reference part image information obtained from a storage module 102 are compared and analyzed by a processing module 101, to obtain change information of a part image of a detected person, and current physical health information of the detected person is obtained on the basis of theory of traditional Chinese medicine, and then the physical health information of the detected person is transmitted to a display module for displaying in the display module, so that a physical condition of the detected person is monitored, and thus an illness may be discovered in time.

Because most diseases are diagnosed by facial features of the detected person in traditional Chinese medicine, in the embodiment of the present disclosure, for example, the part image is a facial image.

On such basis, the processing module 101 is further configured for extracting a facial sub-part image from the facial image according to an accuracy mode indicated by a user instruction, and the facial sub-part image at least include a forehead image, an eye image and a mouth image.

On such basis, the processing module 101 is configured for obtaining change information of the part image of the detected person according to the part image of the detected person and a reference part image in reference part image information obtained from the storage module 102; the obtaining current physical health information of the detected person according to the change information of the part image, may be that: the processing module 101 is configured for obtaining change information of a facial sub-part image of the detected person according to the facial sub-part image extracted from the facial image of the detected person and a reference facial sub-part image extracted from the reference part image; and obtaining current physical health information of the detected person according to the change information of the facial sub-part image.

It should be noted that, an accuracy mode may be displayed in a display module, after a corresponding accuracy mode is selected by a user, the display module may transmit an instruction of the user to the processing module 101, so that the processing module 101 may extract a facial sub-part image according to the selection of the user.

In this way, a detection aimed at demands of the detected person may be performed.

Further, the accuracy mode may include a simple mode, a general mode and an accurate mode.

Figure 2A:
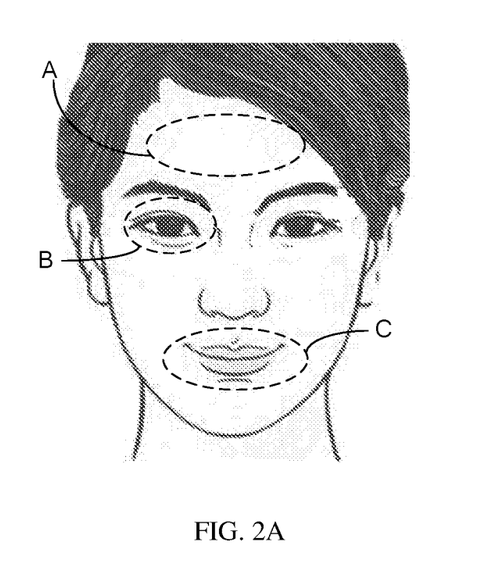
FIG. 2A is a schematic diagram I of extracted parts for facial sub-part images based on an accuracy mode provided by an embodiment of the present disclosure.

Herein, when the accuracy mode indicated by the user instruction is the simple mode, as shown in FIG. 2A, the processing module 101 extracts a forehead image A, an eye image B and a mouth image C from the facial image.

Figure 2B:
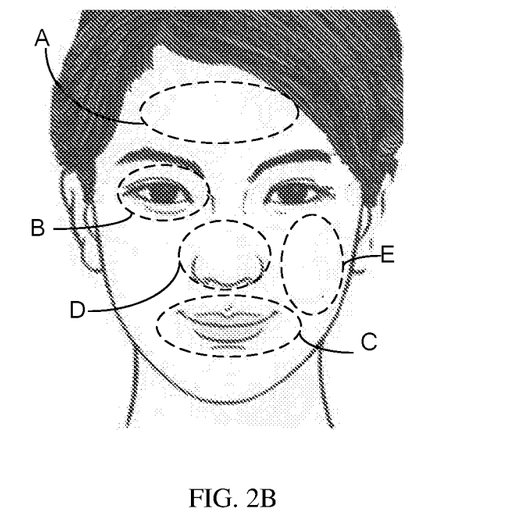
FIG. 2B is a schematic diagram II of extracted parts for facial sub-part images based on an accuracy mode provided by an embodiment of the present disclosure.

When the accuracy mode indicated by the user instruction is the general mode, as shown in FIG. 2B, the processing module 101 extracts a forehead image A, an eye image B, a nose image D, a cheek image E and a mouth image C from the facial image.

When the accuracy mode indicated by the user instruction is the accurate mode, the processing module 101 extracts a forehead image, an eye image, a nose image, a cheek image, a mouth image and a tongue image from the facial image, that is, in this case, the facial image received by the processing module 101 includes the tongue image.

Exemplarily, when the accuracy mode indicated by the user instruction is a simple mode, and the processing module 101 extracts a forehead image, an eye image and a mouth image from the facial image. In this case, when the processing module 101 compares and analyzes the forehead image with a reference forehead image extracted from a reference part image, if it is found that color of the forehead image is lighter than that of the reference forehead image and transverse striations appear, it may be preliminarily determined that the detected person is relatively tired recently; when the processing module 101 compares and analyzes the eye image and the mouth image with a reference eye image and a reference mouth image extracted from the reference part image respectively, if no great change is found, it may be preliminarily determined that the detected person is in normal condition; and after the processing module 101 integrates respective information described above, health information that the detected person is a bit tired may be obtained.

Alternatively, when the accuracy mode indicated by the user instruction is the general mode, the processing module 101 extracts a forehead image, an eye image, a nose image, a cheek image and a mouth image from the facial image. In this case, when the processing module 101 compares and analyzes the forehead image with a reference forehead image extracted from a reference part image, if it is found that color of the forehead image is lighter and transverse striations appears, it may be preliminarily determined that the detected person is relatively tired recently; when the processing module 101 compares and analyzes the eye image with a reference eye image extracted from a reference part image, if it is found that color of the eye image is relatively dark, that is, commonly referred to as a "dark circle", it may be preliminarily determined that the detected person is relatively tired recently or there is potential risk in urinary system, which is because the "dark circle" not only may be caused by fatigue but also be caused by a renal dysfunction in the urinary system; when the processing module 101 compares and analyzes the nose image, the cheek image and the mouth image with a reference eye image, a reference cheek image and a reference mouth image extracted from the reference part image respectively, if no great change is found, it may be preliminarily determined that the detected person is in normal condition; and after the processing module 101 integrates respective information described above, health information that the detected person is a bit tired may be obtained.

It should be noted that, besides the above-described cases where lighter color of the forehead and accompanying with transverse striations, the "black circle" of eye correspond to that the detected person is tired recently or there is potential risk in urinary system, there further are information on a corresponding relationship between the facial image and the related disease as follows:

Anemic countenance: manifested as a haggard face, a pale bloodless skin and mucous membrane.

Hyperthyroidism: often manifested as a wasting face, retractions of two eyelids, exposing white above a black eyeball, exophthalmos, rarely blink and having a shock frightened expression.

Myxedema: manifested as a pale sallow face, puffy eyelids and cheeks, apathetic performance, dull, and having thinning eyebrow and hair.

Rheumatic heart disease: manifested as dark-red cheeks, cyanotic lips, a dark and gloomy tongue, asthma if moving.

Acromegaly: manifested as an increased and forwardly projected lower jaw, thickened ear and nose, high cheekbones, an uplifted superciliary arch, significantly fat and increased lips and tongue.

Hypercortisolism: manifested as a fat round red face, often accompanying itchy sores, increased hair (women having a beard), a fat neck and other features.

Nephrotic edema: in early state of nephropathy, only manifested as swelling of eyelids after getting up in the morning, along with renal damages, may be manifested as a pale face, edema and tight dry skin.

Facial paralysis: manifested as shallow nasolabial groove, a downwards drooped corner of the mouth, the corner of the mouth inclining to a healthy side if any action of teeth. Wherein, for peripheral facial paralysis, there may further be disappearance of fronto-striation on the side, and drooped lower eyelids.

Parkinsonism: common in older people, and manifested as a dull face, expressionless.

Severe dehydration: after losing a large amount of water due to vomiting or diarrhea, manifested as a haggard face, sunken eye sockets, a thin prominent bridge of the nose, raised zygomatic arch which is clearly visible.

Tetanus: after wounded for a few days, manifested as a backwards stretched head, convulsions of four limbs, trismus, facial muscle spasm, like a forced smile.

Dementia face: a patient of cretinism in 9 weeks after born may manifest thick lips, a large tongue and often extending out, mouth often opening with drooling, ugly looks, a pale or yellow face, a short and upturned nose, a collapsed bridge of a nose, a wrinkled forehead.

Endemic cretinism: also known as "cretinism", manifested as a poorly developed face, a stupid face, unresponsive, a big head, a sunken bridge of a nose, two short wide glabellas, a thick and large tongue and often extending out with drooling.

Mongolism: a genetic chromosomal disease, manifested as small eyes, a wide distance between the eyes, a collapsed bridge of a nose, a mouth opening and a tongue extending out with drooling.

Based on the above, for example, the storage module 102 is further configured for storing information on a corresponding relationship between change information of the part image and the physical health information.

On such basis, the processing module 101 is further configured for searching the physical health information corresponding to the change information of the part image in the storage module 102 according to the change information of the part image, and transmitting the found physical health information to a display module for displaying in the display module.

In this way, the physical health information of the detected person may be directly obtained by the processing module 101 without obtaining from, e.g., a network, so that the present disclosure can work in a network-free state.

Figure 3:
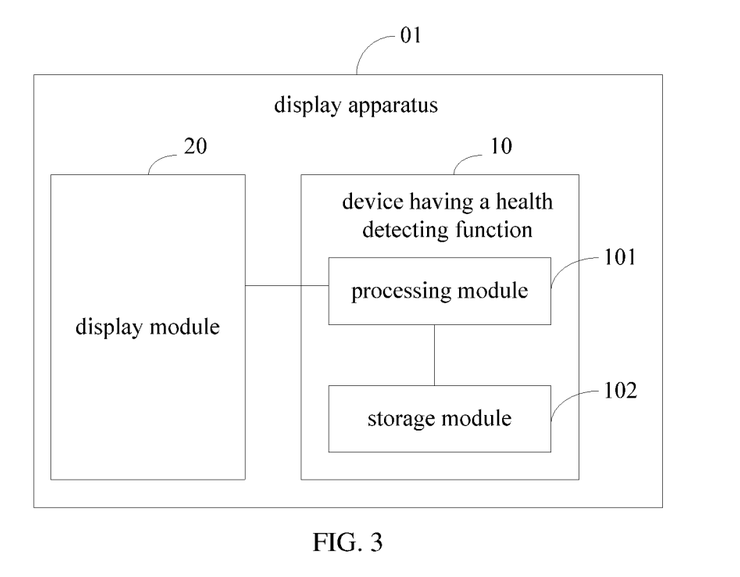
FIG. 3 is a block diagram of a display apparatus provided by an embodiment of the present disclosure.

An embodiment of the present disclose further provides a display apparatus 01; as shown in FIG. 3, the display apparatus 01 includes a display module 20 and the device 10 having the health detecting function described above.

Herein, the display apparatus 01 can be a cell phone, a tablet computer, an E-book device and so on; and the display module 20 can be an a cell phone body, a tablet computer body, an E-book device body and so on; a photographing module 30 configured for acquiring a part image of a detected person and transmitting image information of the detected person including the part image to processing module 101 can be provided in the display apparatus 01, or installed outside the display apparatus 01.

In addition, in practical application, the health detecting function may be preset in the display apparatus 01; after a user instruction for starting the health detecting function is received by the display apparatus, the health detecting function is started.

Since various mobile terminals such as a cell phone are more and more popular, and have become indispensable communication tools in people's lives, if the device 10 having the health detecting function is integrated in the mobile terminal, the device not only may be widely used, but also may display the finally obtained physical health information in time.

Figure 4:
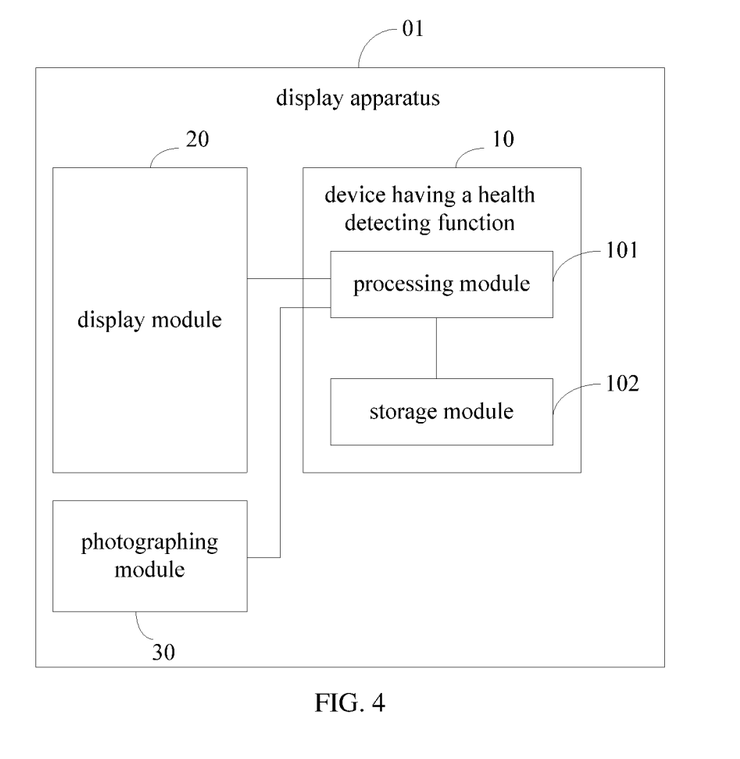
FIG. 4 is a block diagram of a display apparatus provided by an embodiment of the present disclosure.

For example, as shown in FIG. 4, the display apparatus 01 further includes a photographing module 30, that is, the photographing module 30 is provided in the display apparatus 01; the photographing module 30 is configured for acquiring a part image of a detected person, and transmitting image information of the detected person including the part image of the detected person and an acquiring time and an ambient light intensity when acquiring the part image to a processing module 101 of the device 10 having the health detecting function; and the processing module 101 transmits the part image of the detected person to the display module 20 for displaying, and crops redundant information of the part image of the detected person according to a user instruction, and finally transmits image information of the detected person including the cropped part image and the acquiring time and the ambient light intensity to the storage module 102 for storing.

Herein, the part image of a detected person which is acquired by the photographing module 30 often includes some circumstance information around the part of the detected person. Therefore, in the embodiment of the present disclosure, the photographing module 30 of the display apparatus 01 transmits image information of the detected person including the part image of the detected person and the acquiring time and the ambient light intensity to a processing module 101 after acquiring the part image of the detected person, and the processing module 101 parses the image information, and displays the part image of the detected person which is included in image information of the detected person in the display module 20 in a preview mode, and may control the display module 20 to notice a user to crop the acquired part image, so as to delete redundant information, thereby facilitating saving storage space, improving operational speed and recognition accuracy. And then, the processing module 101 transmits image information of the detected person including the cropped part image and the acquiring time and the ambient light intensity to the storage module 102 for storing.

In addition, if the image acquired by the photographing module 30 is not a facial image, the processing module 101 may control the display module 20 to give a notice in text form, for example.

In this way, physical health condition can be detected just by a terminal having a photographing function, the terminal is convenient to carry, and is able to improve user experience on the basis of the prior art.

Figure 5:
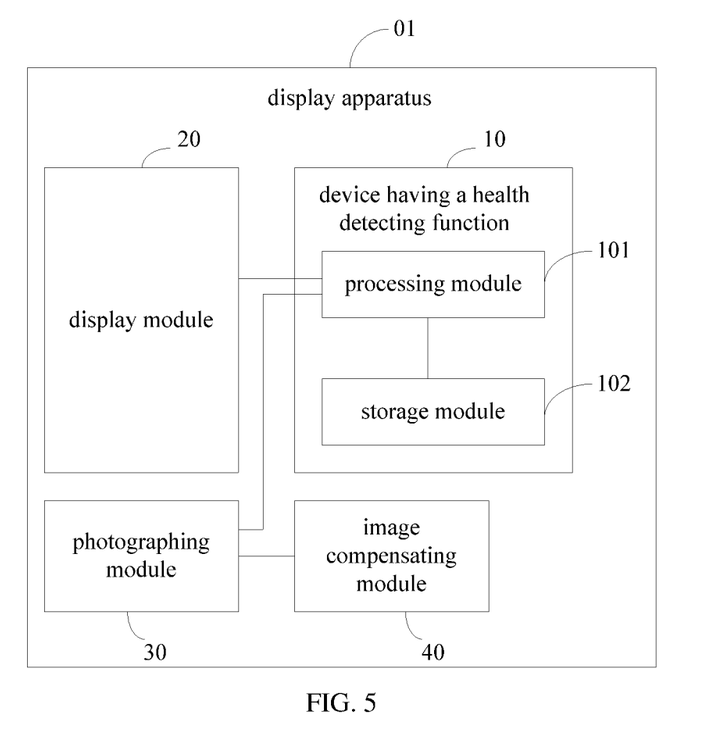
FIG. 5 is a block diagram of a display apparatus provided by an embodiment of the present disclosure.

Further, as shown in FIG. 5, the display apparatus 01 can further include an image compensating module 40; the image compensating module 40 is configured for compensating an ambient light intensity when the photographing module 30 is acquiring the part image of the detected person, if the ambient light intensity when the photographing module 30 acquiring the part image of the detected person is less than a predetermined value.

That is, if the ambient light intensity when the photographing module 30 acquiring the part image of the detected person is relatively dark, current weak ambient light intensity may be compensated by the image compensating module 40, so that the photographing module 30 acquires the part image of the detected person in an ambient light intensity greater than a certain predetermined ambient light intensity.

Figure 6:
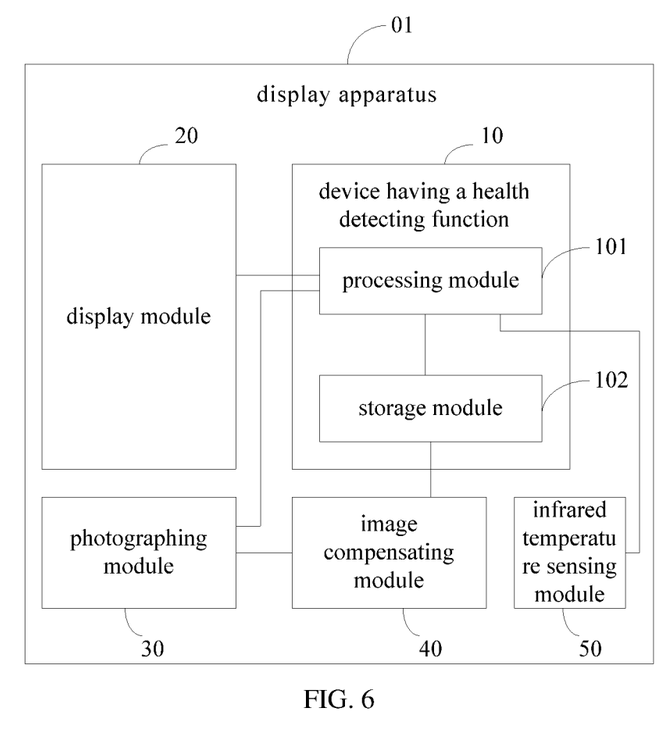
FIG. 6 is a block diagram of a display apparatus provided by an embodiment of the present disclosure.

Based on the above, as shown in FIG. 6, the display apparatus 01 further includes an infrared temperature sensing module 50, and the infrared temperature sensing module 50 is configured for measuring a body temperature of a detected person and transmitting the body temperature to the processing module 101, and the processing module 101 obtains current physical health information of the detected person according to the body temperature of the detected person and the change information of the part image of the detected person.

Figure 7:
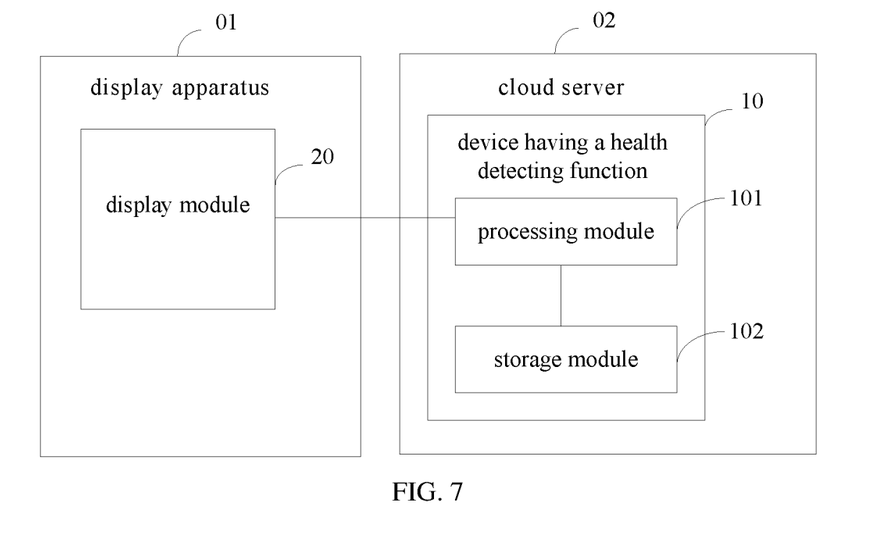
FIG. 7 is a block diagram of a system having a health detecting function provided by an embodiment of the present disclosure.

An embodiment of the present disclosure further provides a system having a health detecting function, as shown in FIG. 7, the system includes a display apparatus 01 and a cloud server 02; wherein, the display apparatus 01 includes a display module 20; and the cloud server 02 includes the device 10 having the health detecting function described above.

In the embodiment of the present disclosure, the device 10 having the health detecting function is integrated into the cloud server 02, which may not occupy storage space and an operational speed of the display apparatus 01.

Figure 8:
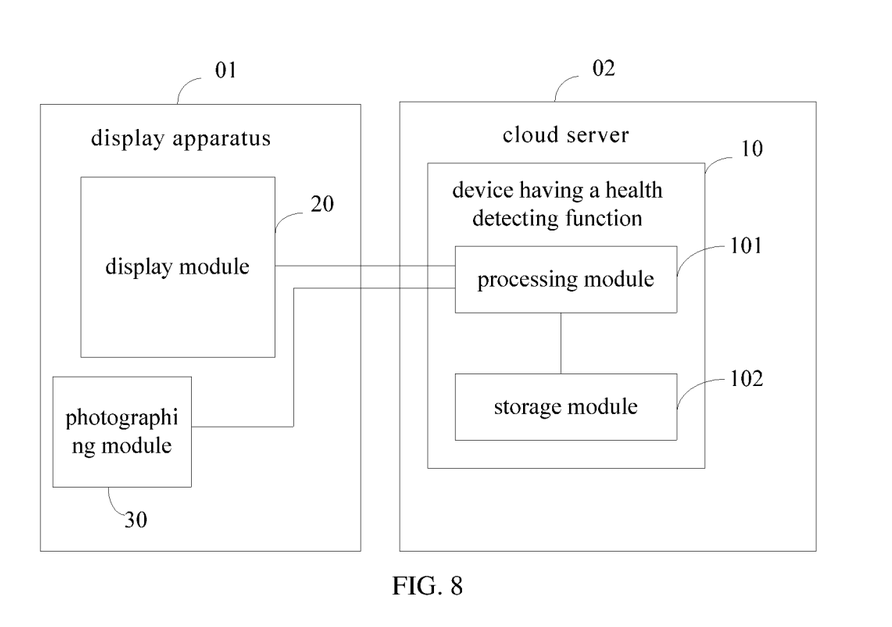
FIG. 8 is a block diagram of a system having a health detecting function provided by an embodiment of the present disclosure.

For example, as shown in FIG. 8, the display apparatus 01 further includes a photographing module 30, and the photographing module 30 is configured for acquiring a part image of a detected person, and transmitting image information of the detected person including the part image of the detected person and an acquiring time and an ambient light intensity when acquiring the part image to a processing module 101 of the device 10 having the health detecting function; and the processing module 101 is configured for transmitting the part image of the detected person to the display module 20 for displaying, and cropping redundant information of the part image of the detected person according to a user instruction, and finally transmits image information of the detected person including the resulting cropped part image and the acquiring time and the ambient light intensity to the storage module 102 for storing.

Herein, the part image of the detected person which is acquired by the photographing module 30 often includes some circumstance information around the part of the detected person. Therefore, in the embodiment of the present disclosure, the photographing module 30 of the display apparatus 01 transmits image information of the detected person including the part image of the detected person and the acquiring time and the ambient light intensity to the processing module 101 after acquiring the part image of the detected person, and the processing module 101 parses the image information, and displays the part image of the detected person included in the image information in the display module 20 in a preview mode, and can control the display module 20 to notice a user to crop the acquired part image, so as to delete redundant information. And then, the processing module 101 transmits image information of the detected person including the cropped part image and the acquiring time and the ambient light intensity to the storage module 102 for storing.

In addition, if the image acquired by the photographing module 30 is not a facial image, the processing module 101 may control the display module 20 to give a notice in text form, for example.

Figure 9:
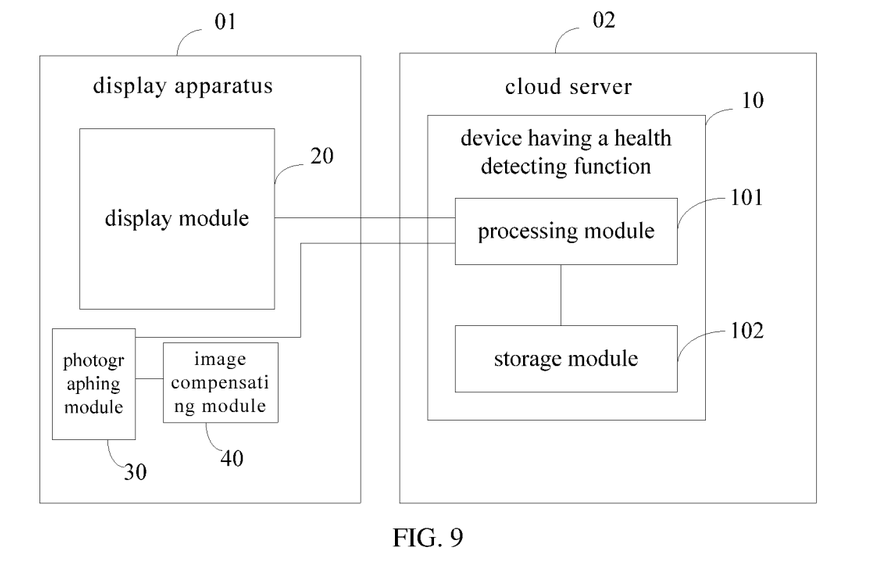
FIG. 9 is a block diagram of a system having a health detecting function provided by an embodiment of the present disclosure.

Further, as shown in FIG. 9, the display apparatus 01 further includes an image compensating module 40; the image compensating module 40 is configured for compensating an ambient light intensity when the photographing module 30 acquiring the part image of the detected person, if the ambient light intensity when the photographing module 30 acquiring the part image of the detected person is less than a predetermined value.

Figure 10:
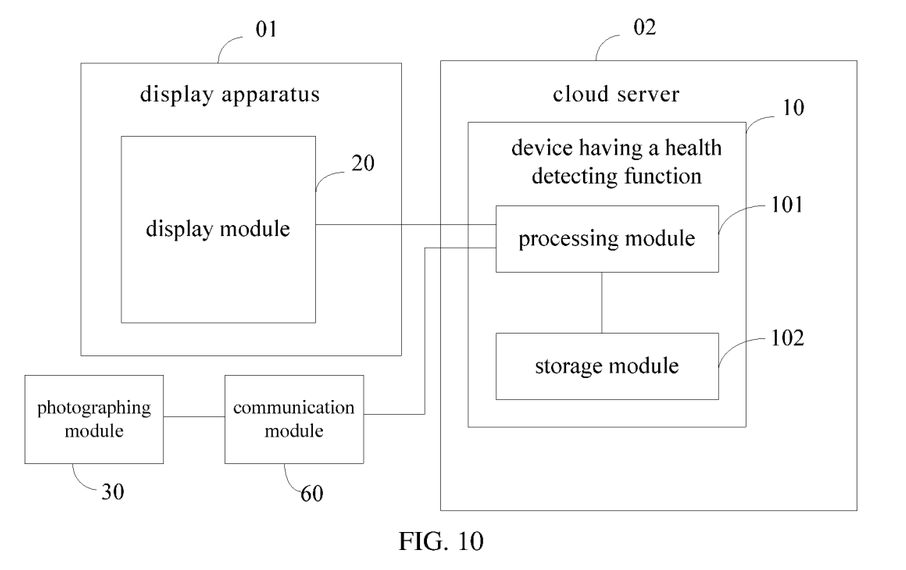
FIG. 10 is a block diagram of a system having a health detecting function provided by an embodiment of the present disclosure.

Optionally, as shown in FIG. 10, the system further includes a photographing module 30 and a communication module 60; the photographing module 30 is configured for acquiring a part image of a detected person, and transmitting image information of the detected person including the part image of the detected person and an acquiring time and an ambient light intensity when acquiring the part image to the processing module 101 of the device 10 having the health detecting function via the communication module 60, and the processing module 101 transmits the part image of the detected person to the display module 20 for displaying, and crops redundant information of the part image of the detected person according to a user instruction, and finally transmits image information of the detected person including the cropped part image and the acquiring time and the ambient light intensity to the storage module 102 for storing.

That is, the photographing module 30 is arranged independent of the display apparatus 01, wherein, the communication module 60 can be data lines for connecting the photographing module 30 and the display apparatus 01 only.

Herein, after the processing module 101 receives image information of the detected person transmitted by the photographing module 30, the processing module 101 parses the image information at first, and then displays the part image of a detected person included therein in the display module 20 in a preview mode, and may control the display module 20 to notice a user to crop the acquired part image, so as to delete redundant information, thereby facilitating saving storage space, improving operational speed and recognition accuracy. And then, the processing module 101 transmits image information of the detected person including the cropped part image and the acquiring time and the ambient light intensity to the storage module 102 for storing.

Figure 11:
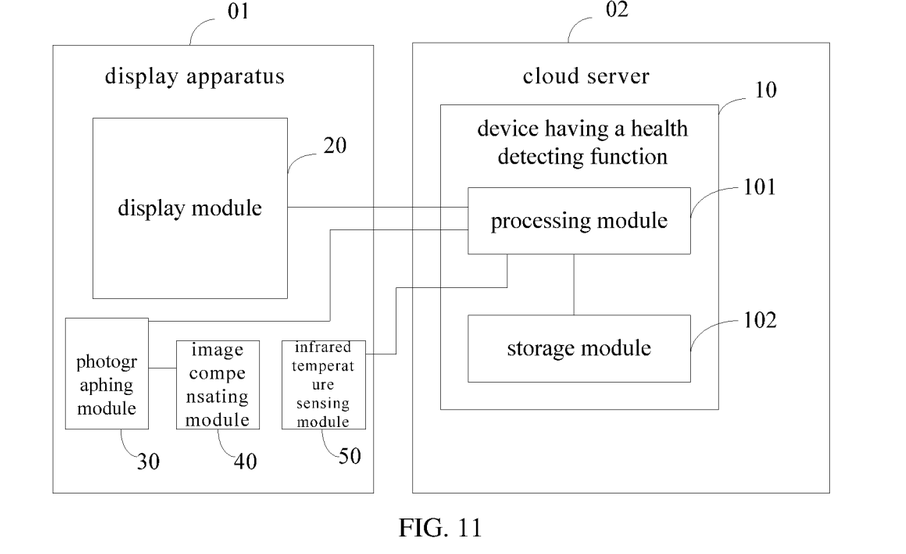
FIG. 11 is a block diagram of a system having a health detecting function provided by an embodiment of the present disclosure.

Based on the above, as shown in FIG. 11, for example, the display apparatus 01 further includes an infrared temperature sensing module 50, and the infrared temperature sensing module 50 is configured for measuring a body temperature of a detected person and transmitting the body temperature to the processing module 101; and the processing module 101 obtains current physical health information of the detected person according to the body temperature of the detected person and the change information of the part image of the detected person.

Figure 12:
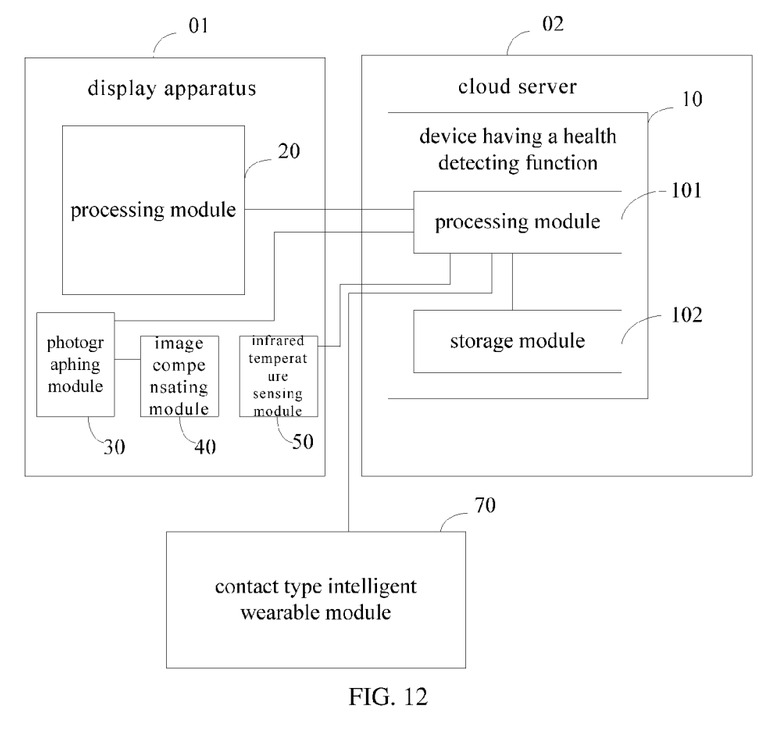
FIG. 12 is a block diagram of a system having a health detecting function provided by an embodiment of the present disclosure.

For example, as shown in FIG. 12, the system further includes a contact type intelligent wearable module 70, and the contact type intelligent wearable module 70 is configured for measuring a heart rate and/or a blood pressure of a detected person and transmitting the heart rate and/or the blood pressure to the processing module 101 of the device 10 having the health detecting function, and the processing module 101 obtains current physical health information of the detected person according to the heart rate and/or the blood pressure of the detected person and the change information of the part image of the detected person.

Figure 13:
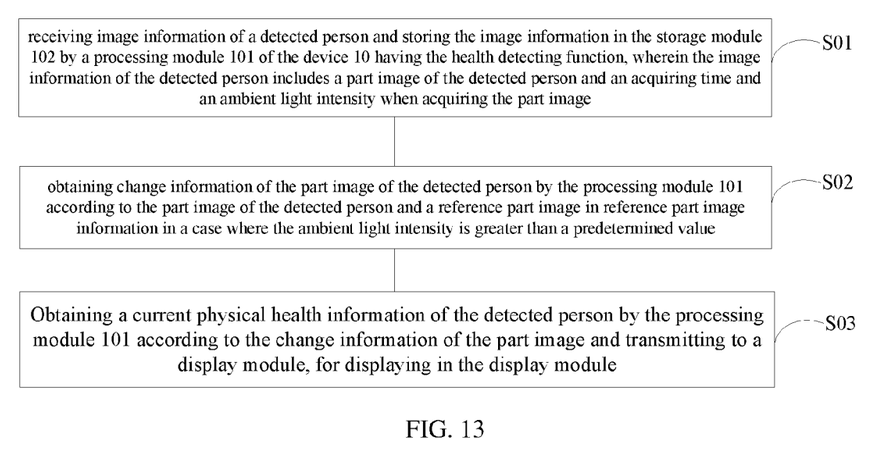
FIG. 13 is a flow chat of a health detecting method provided by an embodiment of the present disclosure.

An embodiment of the present disclosure further provides a health detecting method, and the method may be implemented by the device 10 having the health detecting function described above; as shown in FIG. 13, the method includes steps of:

S01: receiving image information of a detected person and storing the image information in the storage module 102 by a processing module 101 of the device 10 having the health detecting function, wherein the image information of the detected person includes a part image of the detected person and an acquiring time and an ambient light intensity when acquiring the part image.

Herein, the part image of the detected person is not limited, which may be a facial image, or image of four limbs such as a palm, an arm, and a leg and so on.

S02: obtaining change information of the part image of the detected person by the processing module 101 according to the part image of the detected person and a reference part image in reference part image information in a case where the ambient light intensity is greater than a predetermined value.

Wherein, the reference part image information is stored the storage module 102, and the reference part image information includes reference part image of the detected person accumulated before the acquiring time and/or healthy reference part image based on age.

Herein, change information of the part image of the detected person is obtained according to the part image of the detected person and a reference part image, that is, change information of the part image of the detected person is obtained by comparing the part image of the detected person with a reference part image and analyzing.

For example, when the reference part image in the reference part image information includes part images of the detected person accumulated before the acquiring time, and when the part image of the detected person are compared and analyzed with the reference part image in the reference part image information, a healthiest reference part image in the reference part image information may be selected for comparing and analyzing, or one or more reference part images close to the acquiring time may be selected for comparing and analyzing, so as to obtain change information of the part image of the detected person in a certain period. Of course, all reference part images in the reference part image information may be also selected for comparing and analyzing, so as to obtain a curve of changes, based on which current physical health condition of the detected person can be determined.

Of course, the reference part image in the reference part image information can further include healthy reference part images based on ages and further based on gender, and in this case, the part image of the detected person can be directly compared and analyzed with the healthy reference part image.

In addition, the above two comparing and analyzing ways can be performed simultaneously, which will not be repeated here.

It should be noted that, in this step, whether the ambient light intensity is greater than a predetermined value is judged at first; if yes, then change information of the part image of the detected person is obtained according to the part image of the detected person and the reference part image in the reference part image information, and if the ambient light intensity is less than a predetermined value, a notice information can be returned for redetection.

In addition, those skilled in the art should understand that, comparison is based on a same part when comparing and analyzing, and therefore, in the embodiment of the present disclosure, a reference part image in reference part image information and a part image in image information of the detected person are images of a same part.

S03: obtaining current physical health information of the detected person by the processing module 101 according to the change information of the part image and transmitting to a display module, for displaying in the display module.

The embodiment of the present disclosure provides a health detecting method. The change information of the part image of the detected person is obtained by comparing and analyzing the part image of the detected person with the reference part image in the reference part image information, and the current physical health information of the detected person is obtained on the basis of theory of traditional Chinese medicine, and then the physical health information of the detected person is transmitted to a display module for displaying in the display module, so that a physical condition of the detected person is monitored, and thus an illness may be discovered in time.

Because most diseases are diagnosed by facial features of the detected person in traditional Chinese medicine, in the embodiment of the present disclosure, for example, the part image is a facial image.

On such basis, the method further includes: extracting a facial sub-part image from the facial image according to an accuracy mode indicated by a user instruction, wherein, the facial sub-part image at least include a forehead image, an eye image and a mouth image.

That is, all accuracy modes may be displayed by the display module. In response to a corresponding accuracy mode is selected by the user, the accuracy mode is transmitted to a processing module in a form of an instruction, so that the processing module extracts the facial sub-part image according to the accuracy mode indicated by the instruction.

On such basis, obtaining the change information of the part image of the detected person according to the part image of the detected person and a reference part image in reference part image information, for example, is performed by obtaining the change information of a facial sub-part image of the detected person according to the facial sub-part image extracted from the facial image of the detected person and a reference facial sub-part image extracted from the reference part image.

In this way, a detection aimed at demands of the detected person may be performed.

Further, the accuracy modes include a simple mode, a general mode and an accurate mode.

On such basis, the extracting a facial sub-part image from the facial image according to an accuracy mode indicated by a user instruction, for example, includes: extracting a forehead image, an eye image and a mouth image from the facial image if the accuracy mode indicated by the user instruction is the simple mode; extracting a forehead image, an eye image, a nose image, a cheek image and a mouth image from the facial image if the accuracy mode indicated by the user instruction is the general mode; and extracting a forehead image, an eye image, a nose image, a cheek image, a mouth image and a tongue image from the facial image if the accuracy mode indicated by the user instruction is the accurate mode.

Exemplarily, if the accuracy mode indicated by the user instruction is a simple mode, and the processing module 101 extracts a forehead image, an eye image and a mouth image from the facial image. In this case, when the processing module 101 compares and analyzes the forehead image with a reference forehead image extracted from a reference part image, if it is found that color of the forehead image is lighter and transverse striations appear, it may be preliminarily determined that the detected person is relatively tired recently; when the processing module 101 compares and analyzes the eye image and the mouth image with a reference eye image and a reference mouth image extracted from the reference part image respectively, if no obvious change is found, it may be preliminarily determined that the detected person is in normal condition; and after the processing module 101 integrates respective information described above, health information that the detected person is a bit tired may be obtained.

Alternatively, if the accuracy mode indicated by the user instruction is a general mode, the processing module 101 extracts a forehead image, an eye image, a nose image, a cheek image and a mouth image from the facial image. In this case, when the processing module 101 compares and analyzes the forehead image with a reference forehead image extracted from a reference part image, if it is found that color of the forehead image is lighter and transverse striations appear, it may be preliminarily determined that the detected person is relatively tired recently; when the processing module 101 compares and analyzes the eye image with a reference eye image extracted from a reference part image, if it is found that color of the forehead image is relatively dark, that is, commonly referred to as a "dark circle", it may be preliminarily determined that the detected person is relatively tired recently or there is potential risk in urinary system, because a renal dysfunction in the urinary system may also cause the "dark circle" besides that the "dark circle" may be caused by fatigue; when the processing module 101 compares and analyzes the nose image, the cheek image and the mouth image with a reference eye image, a reference cheek image and a reference mouth image extracted from the reference part image respectively, if no great change is found, it may be preliminarily determined that the detected person is in normal condition; and after the processing module 101 integrates respective information described above, health information that the detected person is a bit tired may be obtained.

An embodiment of the present disclosure provides a health detecting method, which, for example, is implemented by a terminal including following modules. The terminal includes: a device having a health detecting function, which includes a processing module 101 and a storage module 102, further includes a display module 20, a photographing module 30, an image compensating module 40 and so on. The health detecting method includes steps of:

S101: receiving information for starting a health detecting function by the terminal.

Herein, in practical application, a health detecting function is preset in the terminal; after the terminal receives an instruction for starting a health detecting function from a user, the terminal starts the health detecting function.

S102: acquiring a facial image of a detected person by the photographing module 30, and the photographing module 30 transmitting image information of the detected person including the part image of the detected person and an acquiring time and an ambient light intensity when acquiring the part image to a processing module 101.

Wherein, it may be determined whether the image acquired is a facial image by a human face detecting algorithm, and the facial image includes a forehead image, an eye image, a nose image, a cheek image and a mouth image and so on.

S103: parsing the image information of the detected person by the processing module 101, and judging whether an ambient intensity is greater than a predetermined value; if yes, performing S104; if no, returns to S101.

S104: displaying the part image of the detected person by the processing module 101 in the display module 20 in a preview mode, and noticing a user to crop redundant information of the part image.

In addition, if the acquired image is not a facial image, the processing module 101 may control the display module 20 to, for example, give a notice in text form, and the user may restart the health detecting function to perform step S101.

S105: transmitting the image information of the detected person including the cropped facial image of the detected person and the acquiring time and the ambient light intensity to the storage module 102 for storing, by the processing module 101.

S106: controlling the display module 20 to display an accuracy mode of health detection by the processing module 101, i.e., to display a simple mode, a general mode and an accurate mode options.

S107: transmitting the accuracy mode selected by a user in a form of an instruction to the processing module 101 by the display module 20 after corresponding accuracy mode, for example, a simple mode, is selected by the user.

S108: extracting a forehead image, an eye image and a mouth image from the facial image based on the current accuracy mode (here, the simple mode) selected by the user.

Herein, if the accuracy mode selected by the user is an accurate mode, then the processing module 101 extracts a facial sub-part image from the facial image, and if no tongue image is extracted, a message is transmitted to a display module 20, and the display module 20, for example, give a notice in text form, and the user may restart the health detecting function to perform step S101.

S109: comparing and analyzing current forehead image, the eye image and the mouth image of the detected person with a reference forehead image, a reference eye image and a reference mouth image extracted from a reference facial image in the reference part image information respectively by the processing module 101, to obtain change information of respective part images of the detected person.

The reference part image information is stored in the storage module; and the reference part image information includes reference part images of the detected person accumulated before the acquiring time and/or healthy reference part images based on ages.

S110: obtaining current physical health information of the detected person by the processing module 101 according to the change information of the respective part images of the detected person, and transmitting to a display module 20.

S111: receiving the current physical health information of the detected person by the display module 20 for displaying.

Although the embodiment of the present disclosure has been described above in great detail with general descriptions and specific embodiments, on the basis of the present disclosure, various changes and improvements may be made, which is apparent to those skilled in the art. Therefore, these modifications or improvements without departing from the spirit of the present disclosure all belong to the protection scope claimed by the present disclosure.

The present application claims priority of Chinese Patent Application No. 201510236951.3 filed on May 11, 2015, the disclosure of which is incorporated herein by reference in its entirety as part of the present application.

The invention claimed is:

1. A device having a health detecting function, comprising a processing module, a storage module, and a photographing module; wherein, the photographing module is configured for acquiring a part image of a detected person and transmitting image information of the detected person including the part image to the processing module, the processing module is configured for receiving image information of the detected person and storing the image information in the storage module, the image information of the detected person including a part image of the detected person and an acquiring time and an ambient light intensity when acquiring the part image; obtaining change information of the part image of the detected person according to the part image of the detected person and a reference part image in reference part image information obtained from the storage module, in a case where the ambient light intensity is greater than a predetermined value; and obtaining current physical health information of the detected person according to the change information of the part image;

the storage module is configured for storing the reference part image information, the reference part image information including a reference part image of the detected person accumulated before the acquiring time and/or a healthy reference part image based on age, wherein, the part image is a facial image, wherein, the processing module is configured for obtaining the change information of the part image of the detected person according to the part image of the detected person and a reference part image in reference part image information obtained from the storage module, and obtaining the current physical health information of the detected person according to the change information of the part image, which includes:

the processing module is configured for comparing and analyzing a forehead image with a reference forehead image extracted from the reference part image to obtain a first change information of the part image, for comparing and analyzing an eye image with a reference eye image extracted from the reference part image to obtain a second change information of the part image, and for determining a potential risk in urinary system at least according to the first change information of the part image and the second change information of the part image.

2. A system having a health detecting function, comprising a display apparatus and a cloud server; wherein, the display apparatus includes a display module;

the cloud server includes the device having the health detecting function according to claim 1, the processing module of the device having the health detecting function being configured for transmitting current physical health information of the detected person to the display module to display.

3. The system according to claim 2, wherein, the display apparatus further includes a photographing module which is configured for acquiring a part image of a detected person, and transmitting image information of the detected person including the part image of the detected person and an acquiring time and an ambient light intensity when acquiring the part image to a processing module of the device having the health detecting function, and the processing module is configured for displaying the part image of the detected person in the display module, and cropping redundant information of the part image of the detected person according to a user instruction, and finally transmitting image information of the detected person including a cropped part image and the acquiring time and the ambient light intensity to the storage module for storing.

4. The system according to claim 3, wherein, the display apparatus further includes an image compensating module;

the image compensating module being configured for compensating the ambient light intensity when the photographing module acquires the part image of the detected person, if the ambient light intensity is less than a predetermined value when the photographing module acquires the part image of the detected person.

5. The system according to claim 2, further comprising a photographing module and a communication module;

the photographing module being configured for acquiring the part image of the detected person, and transmitting image information of the detected person including the part image of the detected person and an acquiring time and an ambient light intensity when acquiring the part image to a processing module of the device having the health detecting function via the communication module, and the processing module is configured for transmitting the part image of the detected person to the display module for displaying, and cropping redundant information of the part image of the detected person according to a user instruction, and finally transmitting image information of the detected person including a cropped part image and the acquiring time and the ambient light intensity to the storage module for storing.

6. The system according to claim 2, wherein, the display apparatus further includes an infrared temperature sensing module, the infrared temperature sensing module being configured for measuring a body temperature of a detected person and transmitting the body temperature to the processing module, and the processing module is configured for obtaining current physical health information of the detected person according to the body temperature of the detected person and the change information of the part image of the detected person.

7. The system according to claim 2, further comprising a contact type intelligent wearable module, the contact type intelligent wearable module being configured for measuring a heart rate and/or a blood pressure of the detected person and transmitting the heart rate and/or the blood pressure to the processing module of the device having the health detecting function, and the processing module is configured for obtaining the current physical health information of the detected person according to the heart rate and/or the blood pressure of the detected person and the change information of the part image of the detected person.

8. A display apparatus, comprising a display module and the device having the health detecting function according to claim 1, wherein, the processing module of the device having the health detecting function transmits current physical health information of a detected person to the display module for displaying.

9. The display apparatus according to claim 8, wherein, the display apparatus further includes a photographing module which is configured for acquiring a part image of a detected person, and transmitting image information of the detected person including the part image of the detected person and an acquiring time and an ambient light intensity when acquiring the part image to the processing module of the device having the health detecting function, and the processing module is configured for making the part image of the detected person display in the display module, and cropping redundant information of the part image of the detected person according to a user instruction, and finally transmitting image information of the detected person including a cropped part image and the acquiring time and the ambient light intensity to the storage module for storing.

10. The display apparatus according to claim 9, further comprising an image compensating module;

the image compensating module being configured for compensating an ambient light intensity when the photographing module acquires the part image of the detected person, if the ambient light intensity is less than a predetermined value when the photographing module acquires the part image of the detected person.

11. The display apparatus according to claim 8, further comprising an infrared temperature sensing module, the infrared temperature sensing module being configured for measuring a body temperature of a detected person and transmitting the body temperature to the processing module, and the processing module obtaining current physical health information of the detected person according to the body temperature of the detected person and the change information of the part image of the detected person.

12. The device according to claim 1, wherein, the accuracy mode include a simple mode, a general mode and an accurate mode;

wherein, when the accuracy mode indicated by a user instruction is the simple mode, the processing module extracts the forehead image, the eye image and a mouth image from the facial image to serve as the facial sub-part image;

when the accuracy mode indicated by the user instruction is the general mode, the processing module extracts the forehead image, the eye image, a nose image, a cheek image and a mouth image from the facial image to serve as the facial sub-part image;

when the accuracy mode indicated by the user instruction is the accurate mode, the processing module extracts the forehead image, the eye image, a nose image, a cheek image, a mouth image and a tongue image from the facial image.

13. The device according to claim 1, wherein, the storage module is further configured for storing information on a corresponding relationship between the change information of the part image and the physical health information;

the processing module is further configured for searching the physical health information corresponding to the change information of the part image in the storage module according to the change information of the part image.

14. The device according to claim 1, wherein, the reference part image in the reference part image information includes reference part images of the detected person accumulated before the acquiring time, all the reference part images is compared and analyzed with so as to obtain a curve of changes, the processing module is configured for obtaining current physical health information of the detected person according to the change information of the part image, which includes: the current physical health condition of the detected person is determined based on the curve of changes.

15. A health detecting method, comprising:

by a photographing module, acquiring a part image of a detected person and transmitting image information of the detected person including the part image to a processing module;

by the processing module and a processing module, receiving image information of the detected person and storing the image information; wherein, the image information of the detected person includes the part image of the detected person and an acquiring time and an ambient light intensity when acquiring the part image;

obtaining change information of the part image of the detected person according to the part image of the detected person and a reference part image in reference part image information in a case where the ambient light intensity is greater than a predetermined value;

obtaining current physical health information of the detected person according to the change information of the part image, and transmitting the current physical health information of the detected person to a display module, so as to display in the display module;

wherein, the reference part image information includes a reference part image of the detected person accumulated before the acquiring time and/or a healthy reference part image based on age, wherein, the part image is a facial image, wherein, the obtaining change information of the part image of the detected person according to the part image of the detected person and a reference part image in reference part image information, includes:

comparing and analyzing a forehead image with a reference forehead image extracted from the reference part image to obtain a first change information of the part image;

comparing and analyzing an eye image with a reference eye image extracted from the reference part image to obtain a second change information of the part image; and determining a potential risk in urinary system at least according to the first change information of the part image and the second change information of the part image.

16. The method according to claim 15, wherein, the accuracy modes include a simple mode, a general mode and an accurate mode;

the extracting a facial sub-part image from the facial image according to an accuracy mode indicated by a user instruction, includes:

extracting the forehead image, the eye image and a mouth image from the facial image when the accuracy mode indicated by the user instruction is the simple mode;

extracting the forehead image, the eye image, a nose image, a cheek image and a mouth image from the facial image when the accuracy mode indicated by the user instruction is the general mode; and extracting the forehead image, the eye image, a nose image, a cheek image, a mouth image and a tongue image from the facial image when the accuracy mode indicated by the user instruction is the accurate mode.

* * * * *